United States Patent [19]

Beucherie et al.

[11] Patent Number: 5,415,860
[45] Date of Patent: May 16, 1995

[54] COSMETIC COMPOSITIONS COMPRISING AQUEOUS EMULSIONS OF ORGANOPOLYSILOXANES

[75] Inventors: Jeannine Beucherie, Massy; Jean-Michel Mercier, Thiais, both of France

[73] Assignee: Rhone-Poulenc Chimie, Courbevoie Cedex, France

[21] Appl. No.: 184,196

[22] Filed: Jan. 18, 1994

Related U.S. Application Data

[63] Continuation of Ser. No. 911,093, Jul. 9, 1992, abandoned.

[30] Foreign Application Priority Data

Jul. 9, 1991 [FR] France ................. 91 09006

[51] Int. Cl.$^6$ ........................ A61K 7/06; A61K 9/107
[52] U.S. Cl. .................... 424/401; 424/70.12; 424/78.03; 424/70.121
[58] Field of Search ............... 424/401, 78.03, 70

[56] References Cited

U.S. PATENT DOCUMENTS 4,855,129  8/1989  Steinbach et al. ............. 424/63

FOREIGN PATENT DOCUMENTS 0268950  6/1980  European Pat. Off. .
0200916  11/1986  European Pat. Off. .
0200916  12/1986  European Pat. Off. .
0268950  1/1988  European Pat. Off. .
0370764  5/1990  European Pat. Off. .
0398177  11/1990  European Pat. Off. .
0737134  9/1955  United Kingdom .
737134  9/1955  United Kingdom .

*Primary Examiner*—Thurman K. Page
*Assistant Examiner*—Peter F. Kulkosky
*Attorney, Agent, or Firm*—Burns, Doane, Swecker & Mathis

[57] ABSTRACT

Fine and stable silicone-in-water emulsions, well suited for cosmetic applications, e.g., for the treatment of hair (shampoo, rinse, etc.) or skin (skin care, dermatology, etc.), include (a) a VHV polydiorganosiloxane having a viscosity of at least $9 \times 10^4$ mPa.s at 25° C., (b) at least one fluid silicone having a viscosity no greater than 50,000 mPa.s. at 25° C. and (c) a sugar glyceride nonionic surface-active agent, and wherein the percentage by weight of such VHV polydiorganosiloxane (a) in the total silicone content (a)+(b) ranges from 5% to 50% and the ratio parts by weight of surface-active agent (c)/parts by weight of water is no greater than 0.7.

14 Claims, No Drawings

COSMETIC COMPOSITIONS COMPRISING AQUEOUS EMULSIONS OF ORGANOPOLYSILOXANES

This application is a continuation of application Ser. No. 07/911,093, filed Jul. 9, 1992, now abandoned.

BACKGROUND OF THE INVENTION

1. Field of the Invention

The present invention relates to novel cosmetic compositions especially well suited for the care of hair or of the skin and comprising certain silicone-in-water emulsions.

2. Description of the Prior Art

The silicones have long been used as raw materials having a wide variety of properties (feel, spreading, inertness and the like) which can advantageously be formulated into cosmetic compositions.

The application of silicone-based aqueous emulsions results in the formation of an invisible hydrophobic film and this property is particularly advantageous for application to skin (providing a non-tacky, nongreasy and soft feel) and for application to hair (untwisting or disentangling effect). In this instance, because of their easy dispersibility, silicone oils are typically used, of low molecular weights and which have a dynamic viscosity at 25° C. well below $5 \times 10^4$ mPa.s. However, because of their superior persistence or longevity, silicone compounds of higher molecular weights and viscosities have appeared to be the silicones of choice, such as oils and resins which have a viscosity at 25° C. of at least $9 \times 10^4$ mPa.s.

Hereinafter, by the expression "VHV compounds" (very high viscosity compounds) are intended the oils and resins exhibiting at 25° C. a viscosity as high as at least $9 \times 10^4$ mPa.s.

Nevertheless, when using VHV silicone compound starting materials, the preparation of aqueous emulsions which are at the same time finely divided and stable presents certain difficulties, which can be overcome, as described in EP-A-0,200,916, on condition, on the one hand, that the VHV compound is used in the form of solution in a volatile silicone, said solution having a viscosity advantageously ranging from 30,000 to $2 \times 10^6$ mPa.s or more and, on the other, that a judicious mixture of three surface-active agents of nonionic type is selected, these having HLB values of 7 to 9 in the case of the first of such agents, from 13 to 15 in the case of the second and equal to or higher than 16 in the case of the third of such agents.

SUMMARY OF THE INVENTION

Accordingly, a major object of the present invention is the provision of novel cosmetic compositions which are in the form of fine and stable aqueous emulsions comprising a VHV silicone compound which has a viscosity of at least $9 \times 10^4$ mPa.s, and which advantageously are formulated from a single surface-active agent instead of three such agents, which to date has characterized the state of this art. By the expression "fine aqueous emulsions" are intended emulsions in which 50% by volume of the dispersed globules have dimensions which are smaller than a number as small as that situated in the range of from 1 to 4 μm.

Briefly, the present invention features cosmetic compositions in the form of silicone/water aqueous emulsions, (I) prepared in an aqueous medium from (a) a VHV polydiorganosiloxane compound having a viscosity at 25° C. of at least $9 \times 10^{-4}$ mPa.s, (b) at least one fluid silicone compound having a viscosity at 25° C. of not more than 50,000 mPa.s, and (c) a sugar glyceride nonionic surface-active agent; and advantageously comprising 100 parts by weight of silicone material (a)+(b), wherein the VHV polydiorganosiloxane (a) constitutes 5% to 50% by weight thereof, 2 to 700 parts by weight of surface-active agent (c), and 3 to 2,000 parts by weight of water, with the proviso that the ratio parts by weight of surface-active agent (c)/parts by weight of water is at most 0.7.

DETAILED DESCRIPTION OF THE PREFERRED EMBODIMENTS OF THE INVENTION

More particularly according to the present invention, the subject cosmetic compositions are prepared from a constituent (a) comprising a VHV polydiorganosiloxane compound containing from 0% to 4% by weight of vinyl groups and whose viscosity at 25° C. is at least $9 \times 10^{-4}$ mPA.s. These VHV compounds are linear polymers of high molecular weight (higher than 90,000 g/mole), in which the polydiorganosiloxane chain consists essentially of recurring units of formula $(R)_2SiO$. This polymer chain is blocked at each end by a structural unit of formula $(R)_3SiO_{0.5}$ and/or a radical of formula OR'. In these formulae:

(i) the symbols R, which may be identical or different, are each a monovalent hydrocarbon radical such as an alkyl radical, for example methyl, ethyl, propyl, octyl or octadecyl, an aryl radical, for example phenyl, tolyl or xylyl, an aralkyl radical such as, for example, benzyl or phenylethyl, a cycloalkyl or cycloalkenyl radical such as, for example, cyclohexyl, cycloheptyl or cyclohexenyl radicals, an alkenyl radical, for example vinyl or allyl radicals, an alkaryl radical, a cyanoalkyl radical such as, for example, a cyanoethyl radical, and a haloalkyl, haloalkenyl or haloaryl radical such as, for example, chloromethyl, 3,3,3-trifluoropropyl, chlorophenyl, dibromophenyl or trifluoromethylphenyl radicals;

(ii) the symbol R' is a hydrogen atom, an alkyl radical having 1 to 4 carbon atoms, or the beta-methoxyethyl radical.

The constituent (a) preferably is a VHV compound whose viscosity at 25° C. is higher than $9 \times 10^4$ mPa.s. and more preferably ranging from $1 \times 10^5$ mPa.s to $20 \times 10^6$ mPa.s and in which at least 60% of the radicals R are methyl radicals. However, the presence, along the polydiorganosiloxane chain, of small amounts of structural units other than $(R)_2SiO$, for example of units of formulae $RSiO_{1.5}$ and/or $SiO_2$ is not excluded, in a proportion not exceeding 2 mol % relative to the number of $(R)_2SiO$ units.

Exemplary units of formulae $(R)_2SiO$ and $(R)_3SiO_{0.5}$ and of the radicals of formula OR' are those of the formulae: $(CH_3)_2SiO_{0.5}$, $CH_3(CH_2=CH)SiO$, $CH_3(C_6H_5)SiO$, $(C_6H_5)_2SiO$, $CH_3(C_2H_5)SiO$, $(CH_3CH_2CH_2)CH_3SiO$, $CH_3(n-C_3H_7)SiO$, $(CH_3)_3SiO_{0.5}$, $(CH_3)_2CH_2=CHSiO_{0.5}$, $CH_3(C_6H_5)_2SiO_{0.5}$, $(CH_3)(C_6H_5)(CH_2=CH)SiO_{0.5}$, —OH, —OCH$_3$, —OC$_2$H$_5$, —O—n—C$_3$H$_7$, —O—iso-C$_3$H$_7$, —O-n-C$_4$H$_9$, —OCH$_2$CH$_2$OCH$_3$.

These VHV compounds are commercially available from silicone manufacturers or can be prepared via a number of conventional techniques.

The cosmetic compositions according to the present invention necessarily also contain a constituent (b) comprising a fluid silicone compound which has a viscosity at 25° C. of not more than 50,000 mPa.s. This fluid silicone compound may be ($b_1$) a linear polydimethylsiloxane, ($b_2$) a cyclic polydimethylsiloxane or ($b_3$) a mixture of a number of species ($b_1$) or ($b_2$) with each other, or a mixture of one or more species ($b_1$) with one or more species ($b_2$). The compound (b) is incorporated in proportions ranging from 50 to 95%, representing the weight percentage of fluid silicone compound (b) in the silicone content (a)+(b).

The linear polydimethylsiloxanes ($b_1$) are widely described in the literature and are commercially available. Preferred are the linear polydimethylsiloxanes which are blocked by a trimethylsiloxy unit at each of the ends of their polymer chain. However, polymers which are otherwise endblocked, for example by a hydroxyl group or by a $(R''O)_3SiO_{0.5}$ unit with $R''$ being an alkyl radical having from 1 to 3 carbon atoms, are also within the ambit of the invention. The linear polymers ($b_1$) are polymers which contain not more than 3% on a numerical basis of siloxane recurring structural units other than dimethylsiloxy units in the polymer chain. By the expression "linear polydimethylsiloxane" is intended, for example, hexamethyldisiloxane.

The cyclic polydimethylsiloxanes ($b_2$) have the following general formula:

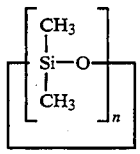
(I)

in which n is a number ranging from 3 to 15. Preferred are cyclic polydimethylsiloxanes in which n ranges from 4 to 7. The species ($b_2$) and a process for the preparation thereof are described in the literature; furthermore, most are available commercially, in particular the species $D_4$ (cyclic polydimethylsiloxane with n=4), $D_5$ (cyclic polydimethylsiloxane with n=5) and the various mixtures thereof.

The viscosity of the fluid silicone compound (b) may vary over wide limits as long as it is not more than 50,000 mPa.s at 25° C. Preferably, such viscosity will be selected within the aforesaid range, taking account, on the one hand, of the viscosity of the VHV compound (a) and, on the other, the respective proportions of the VHV compound (a) and of compound (b), such as to provide a silicone material by mixing (a)+(b) which is sufficiently fluid as to be handleable and easily converted into a fine and stable aqueous emulsion, namely, a silicone material (a)+(b) which has a viscosity lower than $5 \times 10^5$ mPa.s, preferably lower than $1 \times 10^5$ mPa.s and, still more preferably, ranging from 80 to $5 \times 10^4$ mPa.s at 25° C.

The surface-active agent (c) according to the present invention is a sugar glyceride.

The term "sugar glycerides" typically comprehends the mixture of compounds which are obtained directly by transesterification between sucrose and natural or synthetic triglycerides; this mixture contains monoglycerides, diglycerides, unchanged triglycerides (in small amounts), monoesters and diesters of sucrose.

A "triglyceride" is one or more triglycerides of saturated aliphatic fatty acids containing at least 12 carbon atoms, preferably 14 to 22 carbon atoms. It is obviously possible to use a synthetic triglyceride obtained by reaction of glycerol with fatty acids, but it is more advantageous, for economic reasons, to use natural triglycerides, which are mixtures.

Exemplary natural triglycerides include lard, tallow, groundnut oil, butter oil, cottonseed oil, linseed oil, coconut oil, olive oil, palm oil, grapeseed oil, fish oil, soya oil, castor oil, copra oil and rapeseed oil.

The sugar glycerides ($c_1$) of palm, castor, copra or rapeseed oil are the preferred.

The sugar glycerides are in liquid form (sugar castor and rapeseed glycerides) or in the form of pastes of higher or lower consistency which differ commercially in their melting point:

| | |
|---|---|
| Sugar lard glycerides | 47 to 50° C. |
| Sugar tallow glycerides | 50 to 55° C. |
| Sugar palm oil glycerides | 55 to 58° C. |
| Sugar copra oil glycerides | 30 to 32° C. |

A technique which is particularly suitable for preparing these sugar glycerides is described in FR-A-2,463,152.

Various processes can be employed for preparing the silicone/water emulsion, the form in which the cosmetic compositions according to the invention are presented.

For example, when it is desired to prepare an emulsion of the oil-in-water type, two procedures may be carried out, namely:
 (i) either (direct emulsion method No. 1) introducing the silicone material obtained by mixing (a)+(b) into water, the operation being carried out with stirring and at a temperature ranging from room temperature to 60° C., the surface-active agent (c) having been dissolved or dispersed beforehand either in the silicone material or in the water; or
 (ii) (emulsification method No. 2 entailing phase inversion) introducing the water into the silicone material obtained by mixing (a)+(b), the operation being carried out with stirring at a temperature ranging from room temperature to 60° C., the surface-active agent (c) having been dissolved or dispersed beforehand either in the silicone material or in the water; in this second technique a water-in-oil emulsion is first formed and this inverts during the introduction of water when the amount thereof is sufficient.

When it is desired to prepare an emulsion of the water-in-oil type, it is possible to utilize method No. 2 described above, but in this instance with the introduction of the water being terminated prior to the phase inversion.

The aqueous emulsion thus obtained is particularly fine and stable and can then easily be diluted into water.

The cosmetic compositions according to the invention are more particularly intended to be applied to the hair or to the skin; they preferably comprise:
 (i) 100 parts by weight of silicone material (a)+(b) in which the weight percentage of VHV compound (a) in the silicone material constitutes 10% to 30% thereof,
 (ii) 10 to 200 parts by weight of surface-active agent (c), and
 (iii) 40 to 1,200 parts by weight of water, with the proviso that the ratio parts by weight of surface-active agent (c)/parts by weight of water ranges from 0.05 to 0.4.

These compositions may also contain at least one cosmetically acceptable solvent and may be in a thickened or unthickened state of a cream, milk or gel, and may be pressurized as an aerosol in the form of a foam and spray.

Such compositions are more particularly useful as a shampoo, as an after-shampoo composition, as a rinsing agent applicable after shampooing, before or after dyeing and bleaching, before or after permanent waving or hair straightening, as a hairsetting or blow-drying lotion, as a restructuring composition or as an additive to permanent waving, or as a skin care composition.

These compositions can also be employed in dermatology, in which case they contain an agent which is active from a dermatological viewpoint.

The compositions in accordance with the invention may also contain at least one adjuvant selected from among those typically employed in cosmetology, such as fatty substances, for example mineral oils, oils of animal origin and/or fatty esters, perfumes, colorants, preserving agents, hydrating agents, sequestering agents, filtering agents, foaming agents, conditioning agents such as, for example, polymers and, in particular, cationic polymers (polymers containing, for example, a large number of quaternary ammonium groups), anionic polymers (polymers derived, for example, from ethylenically unsaturated carboxylic acids), nonionic or amphoteric polymers or mixtures thereof, thickening agents, structuring agents, foam stabilizers, propellants, or other adjuvants conventionally employed in compositions for the hair or the skin, depending on the particular intended application.

The pH of the compositions according to the invention generally ranges from 4 to 10 and preferably from 4 to 8.5. It can be adjusted by means of alkaline or acid agents, as is well known to this art.

The thickening agents indicated above can be selected, for example, from among the xanthan gums, guar gum or its derivatives, gum arabic or carob gum, sodium alginate, cellulose derivatives and polyacrylic acid derivatives. These thickening agents, when employed, are present in proportions ranging from 0.1% to 30% by weight relative to the total weight of the composition.

The propellants are conventional propellants such as, more particularly, the alkanes, the fluoroalkanes, the chlorofluoroalkanes, or mixtures thereof.

The cosmetically acceptable solvent(s) and/or adjuvant(s) can be incorporated:

(i) either by introducing it (or them) into the compositions of the invention at any time during the preparation of the silicone/water emulsion from the constituents (a), (b) and (c) and water, or (ii) by mixing it (or them) with said emulsion after the latter has been obtained, it being possible for the mixing to be conducted either by incorporating the emulsion into the solvent(s) and/or adjuvant(s), or by incorporating the latter into the emulsion.

It should be appreciated, in accordance with the aforesaid technique (ii), that the cosmetically acceptable adjuvant(s) may conveniently be employed in the form of an aqueous emulsion, prepared in a manner known per se, utilizing a conventional surface-active agent other than the ingredient (c) of the present invention.

It should also be appreciated, also in accordance with such technique (ii) employing an adjuvant(s)/water emulsion, that another adjuvant which can be used can then be a fluid silicone compound selected from among the linear polydimethylsiloxanes ($b_1$) described above. The amount of water which is then introduced by the adjuvant(s)/water emulsion is not critical, as long as, when added to the amount of water introduced by the silicone/water emulsion obtained from the ingredients (a), (b) and (c), it provides a total amount of water in the combination of silicone/water emulsion + adjuvant(s)/water emulsion which satisfies the parameter (II) given above, or does not deviate by more than 20% from the value of the limits indicated.

In like fashion, the amount of silicone which may be introduced by the adjuvant(s)/water emulsion is not critical, as long as, when added to the amount of ingredient (b) introduced by the silicone/water emulsion obtained from the ingredients (a), (b) and (c), it provides a total amount of ingredient (b) in the combination of silicone/water emulsion + adjuvant(s)/water emulsion which also satisfies the parameter (II) given above, or does not deviate by more than 20% from the value of the limits indicated.

The cosmetic treatment according to the present invention essentially entails applying a subject composition either to the hair, depending on the intended use (shampoo, rinsing treatment, hair styling treatment without rinsing), or to the skin (bath or shower products, suntanning products, products for shaving, perfumed lotions, creams or milks, etc.).

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

1. Preparation of a cosmetic composition according to the present invention:

An emulsion of the oil-in-water type was prepared from the following constituents:

(a) 42 parts of a VHV polydimethylsiloxane compound, the linear backbone chain of which was endblocked by a trimethylsiloxy radical at each end and which had a viscosity at 25° C. of $1 \times 10^5$ mPa.s;

(b) 238 parts of a 50/50 by weight mixture of cyclic polydimethylsiloxanes $D_4$ and $D_5$ having a viscosity at 25° C. of 3.6 mPa.s;

(c) 120 parts of sugar castor oil glyceride; this constituent is marketed by Rhone-Poulenc Chimie under the trademark Celynol CO 11; and 600 parts of water.

The silicone material (280 parts) obtained by mixing (a)+(b) had a viscosity at 25° C. of 100 mPa.s.

The sugar glyceride (c) was then poured into the silicone material (a)+(b) subjected to mechanical stirring by means of an Ultra-Turrax apparatus, rotating at 13,500 revolutions/minute. An emulsion of the water-in-oil type was first formed and this inverted when the amount of water required for phase inversion (100 parts) was added. The emulsion of the oil-in-water type thus obtained was milled with the Ultra-Turrax (13,500 revolutions/minute) for 2 minutes. The remaining water (400 parts) was then incorporated slowly with moderate stirring (blade-frame type stirrer rotating at 500 revolutions/minute).

2. Emulsion evaluation tests:

2.1 Stability with temperature: an aliquot fraction of the emulsion prepared as above was divided into two tubes, each of 50-cm³, which were sealed hermetically. One tube was placed into an oven heated to 40° C. while the other tube was stored at room temperature (23° C.). The absence of the following indicia of instability was observed by visual inspection over time: creaming (upward movement of the dispersed globules), sedimentation (downward movement of the dispersed globules) and flocculation (formation of aggregates resulting from the association of a more or less considerable number of globules of the dispersed phase).

The results obtained are reported in the following Table 1:

TABLE 1

| STORAGE TEMPERATURE | 40° C. | 23° C. |
|---|---|---|
| Storage time | 1 month | > 1 month |
| Behavior | stable | stable |

2.2 Particle size of the globules of the dispersed oil phase: the particle size distribution of the emulsion was determined by means of the laser diffraction particle size analyzer marketed under the trademark Sympatec. The measurement was conducted 2 hours after emulsification. Results: The upper limits of the particle size classifications, in the case of 10%, 50% and 80% of globules by volume, were: 1.23 μm (10%), 3.23 μm (50%) and 6 μm (80%), respectively.

EXAMPLES 2 TO 5

1. Preparation of cosmetic compositions according to the present invention:

The procedure described in Example 1, section 1, was repeated, employing the constituents whose nature and proportions (in parts) are reported in Table 2 below:

TABLE 2

| Ingredient Example | (a): VHV compound of Ex. 1 | (b): Mixture D₄ + D₅ of Ex. 1 | (c): Sugar glyceride of Ex. 1 | WATER (1) | (2) | (3) |
|---|---|---|---|---|---|---|
| 2 | 45 | 255 | 40 | 660 | 100 | 100 |
| 3 | 45 | 255 | 80 | 620 | 100 | 100 |
| 4 | 67.5 | 382.5 | 50 | 500 | 100 | 100 |
| 5 | 94.5 | 535.5 | 70 | 300 | 100 | 100 |

(1): Total amount of water; (2): amount of water used for the dispersion of the sugar glyceride; (3): amount of water required for phase inversion.

2. Emulsion evaluation tests:

2.1 Stability with temperature: the results for each Example 2 to 5 are expressed in the same manner as those obtained in Example 1.

2.2 Particle size of the dispersed globules:

TABLE 3

| | % of globules by volume | | |
|---|---|---|---|
| EXAMPLE | 10 | 50 | 80 |
| 2 | 0.93 μm | 2.40 μm | 4.20 μm |
| 3 | 0.94 μm | 2.54 μm | 5.00 μm |
| 4 | 1.05 μm | 2.47 μm | 4.20 μm |
| 5 | 1.24 μm | 2.81 μm | 4.50 μm |

EXAMPLE 6

1. Preparation of a cosmetic composition according to the present invention:

An emulsion of the oil-in-water type was prepared from the following constituents and adjuvant:

(a) 45 parts of a VHV polydimethylsiloxane compound, the linear backbone chain of which was endblocked by a trimethylsiloxy radical at each end and which had a viscosity at 25° C. of $5 \times 10^6$ mPa.s;

(b) 55 parts of a 50/50 by weight mixture of cyclic polydimethylsiloxanes D₄ and D₅ having a viscosity at 25° C. of 3.6 mPa.s;

(c) 40 parts of sugar castor oil glyceride marketed by Rhone-Poulenc Chimie under the trademark Celynol CO 11;

(d) adjuvant, i.e., 2 parts of xanthan gum, marketed by Rhone-Poulenc chimie under the trademark Rhodopol SC; and 658 parts of water.

The silicone material (300 parts) obtained by mixing (a)+(b) had a viscosity at 25° C. of 3,530 mPa.s.

The sugar glyceride was dispersed in 100 parts withdrawn from the aqueous phase formed by the mixture of the xanthan gum (2 parts) and water (658 parts). This dispersion was then poured into the silicone material (a)+(b), subjected to a mechanical stirring as indicated above in Example 1, section 1.

The emulsion of the water-in-oil type which was obtained was inversed by adding, with continued stirring, the required amount of aqueous phase (100 more parts). The emulsion of the oil-in-water type which was formed and the remainder of the aqueous phase (460 parts) were introduced into a colloid mill designated Fryma and the entire mass was milled for 5 minutes under reduced pressure.

2. Emulsion evaluation test:

2.1 Stability with temperature: an aliquot fraction of the emulsion was divided into three tubes, each of 50 cm³. A first tube was stored at room temperature (23° C.); a second tube was stored in an oven heated to 40° C.; the third tube was stored in an enclosure in which the temperature was the subject of temperature cycles (24 hours at 5° C.; 24 hours at 40° C.). After 1 month of storage, and in the case of each of the aforesaid storage conditions, it was not possible by visual inspection to detect any forms of instability such as creaming, sedimentation or flocculation.

2.2 Particle size: the measurement was made using the procedure described in Example 1, section 2.2, on the emulsion stored for 1 month at room temperature. Results: The upper limits of the particle size classifications, in the case of 10%, 50% and 80% of globules by volume, were: 0.93 μm (10%), 2.08 μm (50%) and 4.20 μm (80%), respectively.

EXAMPLE 7

1. Preparation of a cosmetic composition according to the present invention:

An emulsion of the oil-in-water type was prepared from the following constituents and adjuvant:

(a) 45 parts of a VHV polydimethylsiloxane compound the linear backbone chain of which was endblocked by a trimethylsiloxy radical at each end and which had a viscosity at 25° C. of $5 \times 10^6$ mPa.s;

(b) 255 parts of cyclic polydimethylsiloxane D₅ which had a viscosity at 25° C. of 4.7 mPa.s;

(c) 40 parts of sugar rapeseed oil glyceride marketed by Rhone-Poulenc Chimie under the trademark Celynol SGF;

(d) adjuvant, 2 parts of xanthan gum, marketed by Rhone-Poulenc Chimie under the trademark Rhodopol SC; and 658 parts of water.

The emulsion was prepared directly dispersing, at room temperature (23° C.), the silicone material (300 parts), obtained by mixing (a)+(b), in 660 parts of aqueous phase provided by the mixture of the xanthan gum (2 parts) and water (658 parts).

The sugar glyceride (c) had been dispersed beforehand in the silicone material (a)+(b) which had a viscosity at 25° C. of 3,640 mPa.s.

The dispersion of the silicone material in the aqueous phase was carried out with mechanical stirring, the operation being conducted in the Fryma colloid mill. After addition of the silicone material, the mill content was milled for 3 minutes under reduced pressure.

2. Emulsion evaluation test:

2.1 Stability with temperature: after 8 months of storage at room temperature (23° C.), visual inspection did not detect any forms of instability such as creaming, sedimentation or flocculation.

2.2 Particle size: the measurement was made using the procedure described in Example 1, section 2.2, on the emulsion stored for 8 months at room temperature.

Results: The upper limits of the particle size classifications, in the case of 10%, 50% and 80% of the globules by volume, were: 1.29 $\mu$m (10%), 2.74 $\mu$m (50%) and 4.20 $\mu$m (80%), respectively.

EXAMPLE 8

1. Preparation of cosmetic composition according to the present invention, in the form of cream, from constituents (a), (b) and (c), water and adjuvants, via the technique (ii) described above:

1.1 Preparation of the silicone/water emulsion: an emulsion of the oil-in-water type was prepared from the following constituents and adjuvants:
- (a) 45 parts of a VHV polydimethylsiloxane compound, the linear backbone chain of which was endblocked by a trimethylsiloxy radical at each end and which had a viscosity at 25° C. of $5 \times 10^6$ mPa.s;
- (b) 255 parts of a 50/50 by weight mixture of cyclic polydimethylsiloxanes $D_4$ and $D_5$ having a viscosity at 25° C. of 3.6 mPa.s;
- (c) 40 parts of sugar castor oil glyceride marketed by Rhone-Poulenc Chimie under the trademark Celynol CO 11;
- (d) adjuvant, i.e., 2 parts of xanthan gum marketed by Rhone-Poulenc Chimie under the trademark Rhodopol SC; and 10 parts of propylene glycol (or 1,2-dihydroxy propane); and
- 648 parts of water.

To prepare the desired emulsion, the sugar glyceride was first dispersed in the silicone material (300 parts) obtained by mixing (a)+(b); said silicone material had a viscosity at 25° C. of 3530 mPa.s. Into the sugar glyceride/silicone dispersion were then introduced 100 parts of the aqueous phase constituted by the mixture of the xanthan gum (2 parts), propylene glycol (10 parts) and water (648 parts); this introduction was carried out with mechanical stirring (Ultra-Turrax rotating at 13,500 revolutions/minute). The emulsion of the water-in-oil type thus obtained was inverted by adding, with continued stirring, the required amount of aqueous phase (100 more parts). The emulsion of the oil-in-water type which was formed was milled with the Ultra-Turrax (13,500 revolutions/minute) for 5 minutes. The residual aqueous phase (460 parts) was added with moderate stirring (blade-frame stirrer rotating at 500 revolutions/minute).

1.2 Preparation of the cream: the cream was formulated by introducing:
- (i) 15 parts of the silicone/water emulsion described above in section 1.1.
- (ii) into 85 parts of a thick adjuvants/water emulsion having an aqueous continuous phase, maintained at 50° C., the operation being carried out with mechanical stirring (blade-frame stirrer rotating at 500 revolutions/minute.

The adjuvants/water emulsion was prepared by mixing water (71 parts) and the following adjuvants: 10 parts of liquid paraffin, 3 parts of stearic acid and 16 parts of a mixture of polyoxyethylene glycol stearates marketed by Gattefosse under the trademark Tefose.

2. Particle size of the globules of the dispersed oily phase of the cream:

The measurement was carried out according to the procedure described in Example 1, section 2.2.

It was determined that 50% by volume of the globules dispersed in the cream were of sizes smaller than 3.5 $\mu$m.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A silicone-in-water emulsion suited for cosmetic applications, comprising a fine and stable emulsion, in water, of (a) a VHV polydiorganosiloxane having a viscosity of at least $9 \times 10^4$ mPa.s at 25° C., (b) at least one fluid silicone having a viscosity no greater than 50,000 mPa.s at 25° C. and (c) a sugar glyceride nonionic surface-active agent, wherein the percentage by weight of said VHV polydiorganosiloxane (a) in the total silicone content (a)+(b) ranges from 5% to 50% and the ratio parts by weight of surface-active agent (c)/parts by weight of water is between about 0.05 and 0.7.

2. The silicone-in-water emulsion as defined by claim 1, comprising 100 parts by weight of total silicone (a)+(b), 2 to 700 parts by weight of surface-active agent (c), and 3 to 2,000 parts by weight of water.

3. The silicone-in-water emulsion as defined by claim 1, said VHV polydiorganosiloxane consisting essentially of recurring structural units of formula $(R)_2SiO$ and being endblocked by a structural unit of formula $(R)_3SiO_{0.5}$ and/or a radical of formula $OR'$, in which formulae the radicals R, which may be identical or different, are each a monovalent hydrocarbon, alkyl, aryl, aralkyl, cycloalkyl, cycloalkenyl, alkenyl, alkaryl, cyanoalkyl, haloalkyl, haloalkenyl or haloaryl radical; and the radical $R'$ is a hydrogen atom, an alkyl radical having from 1 to 4 carbon atoms or the beta-methoxyethyl radical.

4. The silicone-in-water emulsion as defined by claim 3, said VHV polydiorganosiloxane (a) having a viscosity at 25° C. ranging from $1 \times 10^5$ to $20 \times 10^6$ mPa.s and in which at least 60% of the radicals R are methyl radicals.

5. The silicone-in-water emulsion as defined by claim 1, said silicone (b) comprising ($b_1$) a linear polydimethylsiloxane, ($b_2$) a cyclic polydimethylsiloxane, or ($b_3$) a mixture of a plurality of species ($b_1$) or ($b_2$), or a mixture of one or more species ($b_1$) with one or more species ($b_2$).

6. The silicone-in-water emulsion as defined by claim 5, comprising a linear polydimethylsiloxane ($b_1$) end-blocked by trimethylsiloxy radicals at each end of its polymer chain.

7. The silicone-in-water emulsion as defined by claim 5, comprising a cyclic polymethylsiloxane ($b_2$) having from 4 to 7 silicon atoms.

8. The silicone-in-water emulsion as defined by claim 1, the total silicone content (a)+(b) having a viscosity of less than $1 \times 10^5$ mPa.s at 25° C.

9. The silicone-in-water emulsion as defined by claim 1, said sugar glyceride nonionic surface-active agent (c) comprising a sugar palm, castor, copra or rapeseed oil glyceride.

10. The silicone-in-water emulsion as defined by claim 1, further comprising at least one cosmetically acceptable solvent.

11. The silicone-in-water emulsion as defined by claim 8, further comprising at least one cosmetically acceptable fatty substance, perfume, colorant, preservative, hydrating agent, sequestering agent, sunscreen, foaming agent, conditioning agent, thickening agent, structuring agent, foam stabilizer or propellant.

12. The silicone-in-water emulsion as defined by claim 1, comprising a shampoo or hair rinse.

13. The silicone-in-water emulsion as defined by claim 1, comprising a skin care composition.

14. The silicone-in-water emulsion as defined by claim 1, having a pH ranging from 4 to 8.5.

* * * * *